United States Patent
Sano et al.

(10) Patent No.: US 11,697,004 B2
(45) Date of Patent: Jul. 11, 2023

(54) METHOD OF MANUFACTURING A BALLOON CATHETER

(71) Applicant: NIPRO CORPORATION, Osaka (JP)

(72) Inventors: Yoshihiko Sano, Osaka (JP); Yasushi Ooyama, Osaka (JP); Katsuhiro Hiejima, Osaka (JP)

(73) Assignee: NIPRO CORPORATION, Osaka (JP)

( * ) Notice: Subject to any disclaimer, the term of this patent is extended or adjusted under 35 U.S.C. 154(b) by 603 days.

(21) Appl. No.: 16/793,164

(22) Filed: Feb. 18, 2020

(65) Prior Publication Data

US 2020/0179662 A1 Jun. 11, 2020

Related U.S. Application Data

(63) Continuation of application No. 15/554,725, filed as application No. PCT/JP2016/064121 on May 12, 2016, now abandoned.

(30) Foreign Application Priority Data

May 15, 2015 (JP) ................................. 2015-099712

(51) Int. Cl.
*A61M 25/10* (2013.01)
*A61F 2/958* (2013.01)
(Continued)

(52) U.S. Cl.
CPC ......... *A61M 25/1036* (2013.01); *A61F 2/958* (2013.01); *A61M 25/10* (2013.01);
(Continued)

(58) Field of Classification Search
CPC .............. A61M 25/1036; A61M 25/10; A61M 25/1018; A61M 25/1029; A61M 25/0053;
(Continued)

(56) References Cited

U.S. PATENT DOCUMENTS 8,538,515 B2* 9/2013 Atanasoska ............ A61N 1/327
604/509
2003/0028210 A1 2/2003 Boyle et al.
(Continued)

FOREIGN PATENT DOCUMENTS

JP H05-084304 4/1993
JP 2000140118 A 5/2000
(Continued)

OTHER PUBLICATIONS

International Search Report for PCT/JP2016/064121 dated Jun. 14, 2016 (4 pages.).
(Continued)

*Primary Examiner* — Julian W Woo
(74) *Attorney, Agent, or Firm* — Jason Shapiro; Devlin Law Firm LLC

(57) ABSTRACT

To provide a new balloon catheter enabling formation of, with high dimensional accuracy and excellent shape adaptability with respect to a balloon, an additional structure such as a blade and a reinforcement member to be additionally provided to the balloon. In this balloon catheter 10 provided with an expandable/contractible balloon 14 on the distal end side of a catheter 12, an additional structure 36 having a prescribed pattern is formed through electroforming or the like directly onto an inner circumferential surface 34 and/or an outer circumferential surface 82 of the balloon 14.

12 Claims, 5 Drawing Sheets

(51) Int. Cl.
*A61M 25/00* (2006.01)
*B29L 31/00* (2006.01)

(52) U.S. Cl.
CPC ...... *A61M 25/104* (2013.01); *A61M 25/1018* (2013.01); *A61M 25/1029* (2013.01); *A61F 2002/9583* (2013.01); *A61M 25/0029* (2013.01); *A61M 25/0053* (2013.01); *A61M 2025/0034* (2013.01); *A61M 2025/1031* (2013.01); *A61M 2025/1084* (2013.01); *A61M 2025/1086* (2013.01); *B29L 2031/7543* (2013.01)

(58) Field of Classification Search
CPC .. A61M 2025/0034; A61M 2025/1031; A61M 2025/1084; A61M 2025/1086; A61F 2/958
See application file for complete search history.

(56) References Cited

U.S. PATENT DOCUMENTS

| | | | |
|---|---|---|---|
| 2006/0085023 | A1 | 4/2006 | Davies et al. |
| 2008/0183132 | A1 | 7/2008 | Davies et al. |
| 2011/0046711 | A1 | 2/2011 | Degen |
| 2012/0259193 | A1 | 10/2012 | Gunday et al. |
| 2013/0138081 | A1 | 5/2013 | Stankus et al. |
| 2014/0155927 | A1 | 6/2014 | Burton |

FOREIGN PATENT DOCUMENTS

| | | |
|---|---|---|
| JP | 2003507096 A | 2/2003 |
| JP | 2007-006941 | 1/2007 |
| JP | 2008-509749 A | 4/2008 |
| JP | 2008-519654 A | 6/2008 |
| JP | 2009-513299 A | 4/2009 |
| JP | 2014-516293 A | 7/2014 |
| JP | 2014200330 A | 10/2014 |
| WO | 2012-029109 | 3/2012 |

OTHER PUBLICATIONS

Notification of Transmittal of Translation of the International Preliminary Report on Patentability for PCT/JP2016/064121 dated Nov. 30, 2017, including International Preliminary Reporton Patentability dated Nov. 21, 2017 and Translation of Written Opinion of the International Searching Authority dated Jun. 14, 2016 (7 pages.).
Extended European Search Report issued in European U.S. Appl. No. 16/796,388 3 dated Nov. 29, 2018, (7 pages.).
Notice of Reasons for Refusal received in Japanese application No. 2017-519163, dated Jul. 1, 2020 (11 pages).
Notification of the Second Office Action received in Chinese application No. 201680008115.2, dated Jun. 19, 2020 (10 pages).
European Office Action received in European Patent Application No. 16796388.3, dated Aug. 19, 2020 (7 pages).
Third Office Action issued in Chinese Patent Application No. 201680008115.2, dated Nov. 11, 2020 (11 pages).
Office Action issued in Japanese Patent Application No. 2017-519163, dated Feb. 2, 2021 (7 pages).
Notice of Reasons for Refusal issued in related Japanese Application No. 2017-519163, dated Jan. 8, 2020, with English translation (8 pages.).
First Office Action issued in related Chinese Patent Application No. 201680008115.2, dated Dec. 3, 2019, with English translation (14 pages).

* cited by examiner

METHOD OF MANUFACTURING A BALLOON CATHETER

CROSS REFERENCE TO RELATED APPLICATIONS

This application is a continuation of U.S. patent application Ser. No. 15/554,725, filed on Aug. 31, 2017, which is a 371 National Stage of International Application No. PCT/JP2016/064121, filed on May 12, 2016, and claims priority under 35 U.S.C. § 119 to Japanese Application No. JP2015-099712, filed on May 15, 2015, all of which are incorporated by reference herein in their entirety.

TECHNICAL FIELD

The present invention relates to a balloon catheter that is a medical instrument including a balloon provided on a distal end side of a shaft which is used for various treatments such as percutaneous angioplasty and stent operation by being inserted in a somatic lumen like a blood vessel.

BACKGROUND ART

A balloon catheter has been known as one medical instrument for transdermally curing a lesion location in a lumen like a blood vessel. As is disclosed in Japanese Unexamined Patent Publication No. JP-A-HOS-084304 (Patent Document 1), Japanese Domestic Publication of International Patent Application No. JP-A-2008-509749 (Patent Document 2), Japanese Domestic Publication of International Patent Application No. JP-A-2008-519654 (Patent Document 3), and the like, for the balloon catheter, a balloon is provided on a distal end side of a shaft that should be inserted in the lumen from the outside of a body. The balloon is expandable and contractible by supply and discharge operation of a pressurized fluid at a proximal end side of the shaft positioned outside the body. This balloon catheter enables some cures e.g., expansion of a stenosis portion of the blood vessel using the balloon, stent delivering and indwelling in relation to the expanded stenosis portion, and slitting in a calcified portion with a blade arranged on the outer circumference of the balloon.

The required characteristics for the balloon of the balloon catheter differ depending on specific purposes etc. For example, when a great force is required in order to expand the lumen, the wall of the balloon needs great pressure resistance. For slitting in the calcified portion of the blood vessel, it is necessary to provide a blade of high rigidity on the outer circumference of the balloon.

For responding to these requests, it is conceivable that the pressure resistance is improved by material change or thickening of the balloon, or that a blade part in a projection shape is integrally formed on the outer circumference by shape change of the balloon, for example.

However, by improving the pressure resistance through material change or thickening of the balloon, or by forming the blade part through shape change of the balloon, or the like, the required characteristics may be difficult to sufficiently attain. For example, the balloon may be so thickened and thus hardened for realizing the required pressure resistance as to deteriorate crossability through the lesion location etc.

Japanese Domestic Publication of International Patent Application No. JP-A-2009-513299 (Patent Document 4) discloses a structure of the balloon catheter wherein a resin-reinforced tube having holes pierced on the circumference wall thereof is inserted in the balloon for reinforcement. However, this balloon catheter is difficult to manufacture, because the manufacture needs not only a mold and special facilities for forming the resin-reinforced tube independently from the balloon, but also precise dimension matching of the balloon and the resin-reinforced tube. Since the resin-reinforced tube must be pierced on the circumference wall of the tube body, the degree of freedom for shape is small, so that it is also difficult to highly achieve various characteristics as required for the balloon catheter.

BACKGROUND ART DOCUMENT

Patent Document

Patent Document 1: JP-A-HOS-084304
Patent Document 2: JP-A-2008-509749
Patent Document 3: JP-A-2008-519654
Patent Document 4: JP-A-2009-513299

SUMMARY OF THE INVENTION

Problem the Invention Attempts to Solve

The present invention was made against the background described above, and the problem to be solved is to provide a balloon catheter with a novel structure capable of highly meeting various requests depending on the purposes with a great degree of freedom.

Means for Solving the Problem

A first mode of the present invention provides a balloon catheter including a balloon provided on a distal end side of a shaft, characterized in that: an additional structure having a prescribed pattern is provided on a surface of at least one of an inner circumferential surface and an outer circumferential surface of the balloon by being directly formed thereon.

In the balloon catheter of the structure according to this mode, the additional structure is directly formed on the surface of the balloon, whereby it is possible to provide the additional structure precisely corresponding to the balloon shape. The shape of the additional structure can be set on the surface of the balloon with a great degree of freedom, without limitation to the tube shape like the conventional structure disclosed in Patent Document 4. Therefore, it becomes also possible to advantageously realize the required characteristics for the balloon catheter.

A second mode of the present invention provides the balloon catheter according to the first mode, wherein the additional structure is formed on the inner circumferential surface of the balloon.

In the balloon catheter of the structure according to this mode, the additional structure is directly formed on the inner circumferential surface of the balloon. This makes it possible to form so-called high pressure resistant balloon with improved pressure resistance performance, e.g., of about 24 atm for coronary artery, while preventing direct contact of the additional structure with a body tissue like a blood vessel. In the balloon catheter of the structure according to this mode, even if the additional structure falls off the balloon, the additional structure will stay inside the catheter, with no risk of damaging the vessel wall.

A third mode of the present invention provides the balloon catheter according to the first or second mode, wherein the additional structure is formed by at least one of thermal spraying and vacuum deposition.

A fourth mode of the present invention provides the balloon catheter according to the first or second mode, wherein the additional structure is formed by at least one of electroforming and etching.

In the balloon catheter of the structure according to the third or fourth mode of the present invention, by using such arts as electroforming, it is possible to form the additional structure with a higher dimension accuracy for shape and thickness.

A fifth mode of the present invention provides the balloon catheter according to any of the first to fourth modes, wherein the additional structure has a tubular mesh shape that is continuous in a circumferential direction of the balloon.

In the balloon catheter of the structure according to this mode, by adopting the mesh shape of additional structure, it is possible to permit deformation of the balloon, and keep good softness, and reinforce the circumference wall of the balloon, thereby improving the pressure resistance performance. The mesh shape of this mode involves various embodiments wherein linear bodies connect or intersect to provide an opening. For example, it is possible to use a structure having a plurality of spiral linear bodies intersecting one another, a stent-formed structure having linear bodies that extend in the circumferential direction while meandering in a wave shape or a lightning shape which are partially connected in the axial direction, and the like.

Note that it is possible as well to adopt the mesh-shaped additional structure according to the present mode, in addition to a different additional structure of another mode that is formed on the inner circumferential surface or the outer circumferential surface of the balloon according to a sixth mode etc. as will be described later.

A sixth mode of the present invention provides the balloon catheter according to any of the first to fifth modes, wherein the additional structure has a linear shape that is continuous in a lengthwise direction of the balloon.

In the balloon catheter of the structure according to this mode, it is possible to have the additional structure project on the outer circumferential surface of the balloon so as to constitute a blade. This blade constituted by the additional structure may be formed of a rigid material like a metal which is different from that of the balloon and it can be preferably used as a cutting balloon catheter or the like. For the balloon catheter of the structure according to this mode, it is also possible to make the additional structure project on the inner circumferential surface of the balloon, and it becomes easy to form so-called high pressure resistant balloon with improved pressure resistance performance, e.g., of about 24 atm for coronary artery.

A seventh mode of the present invention provides the balloon catheter according to any of the first to sixth modes, wherein the additional structure is deformable due to expansion and contraction of the balloon.

In the balloon catheter of the structure according to this mode, under either expanding or contracting state of the balloon, such action as reinforcement for the balloon can be more effectively kept and exhibited. For permitting the deformation of the additional structure, the additional structure itself can be formed of a material that can undergo deformation like extension and contraction. Alternatively, the additional structure can have a curved shape so as to be a structure allowed to undergo deformation like extension and contraction.

An eighth mode of the present invention provides the balloon catheter according to any of the first to seventh modes, wherein the additional structure is secured on the surface of the balloon.

In the balloon catheter of the structure according to this mode, the additional structure is secured on the balloon, thereby enabling prevention of damages on the additional structure, as well as improvement in reinforcing effect for the balloon, for example. Especially in the present invention, the additional structure is formed directly on the inner circumferential surface or the outer circumferential surface of the balloon. This makes it easier to readily and firmly realize the attachment structure of the additional structure to the balloon, by comparison with a case of separate formation and later attachment.

Effect of the Invention

According to the present invention, in the balloon catheter, the additional structure precisely corresponding to the balloon shape can be provided with a great degree of freedom under no limitation to the tube shape etc. This additional structure can meet various characteristics required for the balloon catheter, e.g., pressure resistance performance and strength of the balloon, setting of the blade with respect to the outer circumferential side of the balloon.

EMBODIMENTS FOR CARRYING OUT THE INVENTION

The embodiment of the present invention will be described below in reference to the drawings.

Figure 1:
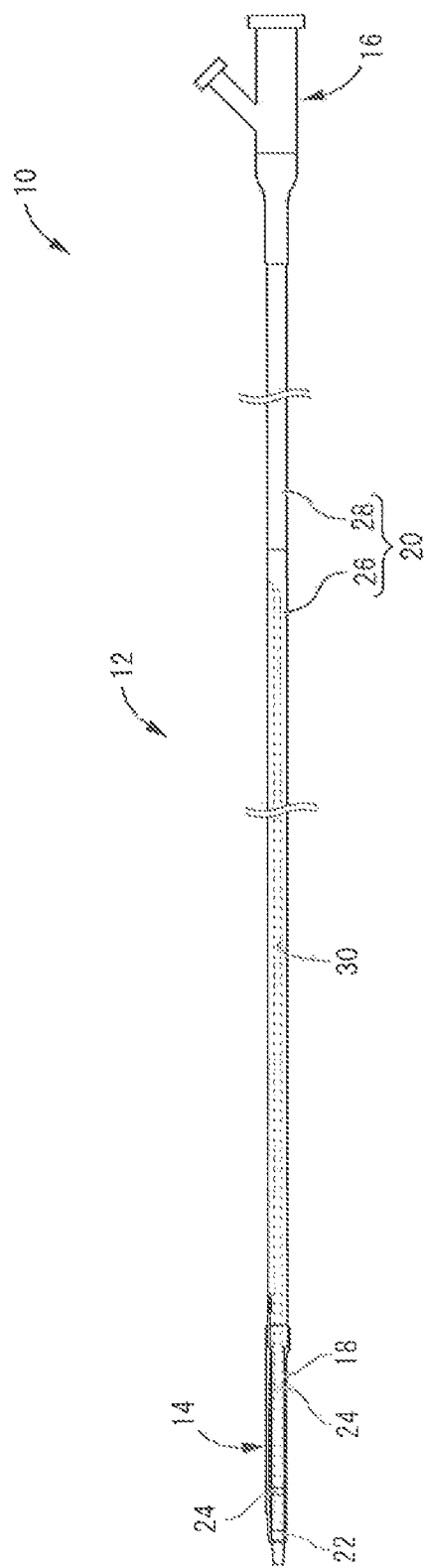
FIG. 1 is a general view suitable for explaining an outline structure of a balloon catheter as a first embodiment of the present invention.

First, FIG. 1 shows a balloon catheter 10 as a first embodiment of the present invention. This balloon catheter 10 has a long catheter 12, wherein a balloon 14 is provided on the distal end side of the catheter 12 (the left side in FIG. 1), while a hub 16 is provided on the proximal end side of the catheter 12 (the right side in FIG. 1). The distal end side of the catheter 12 is inserted into a blood vessel through a part of a human body such as a wrist or a thigh until it reaches a treatment location like a coronary artery, and then, the balloon 14 is swollen. By so doing, it is possible to perform a treatment of expanding the stenosis portion in the blood vessel to recover normal blood flow, and the like.

Figure 2:
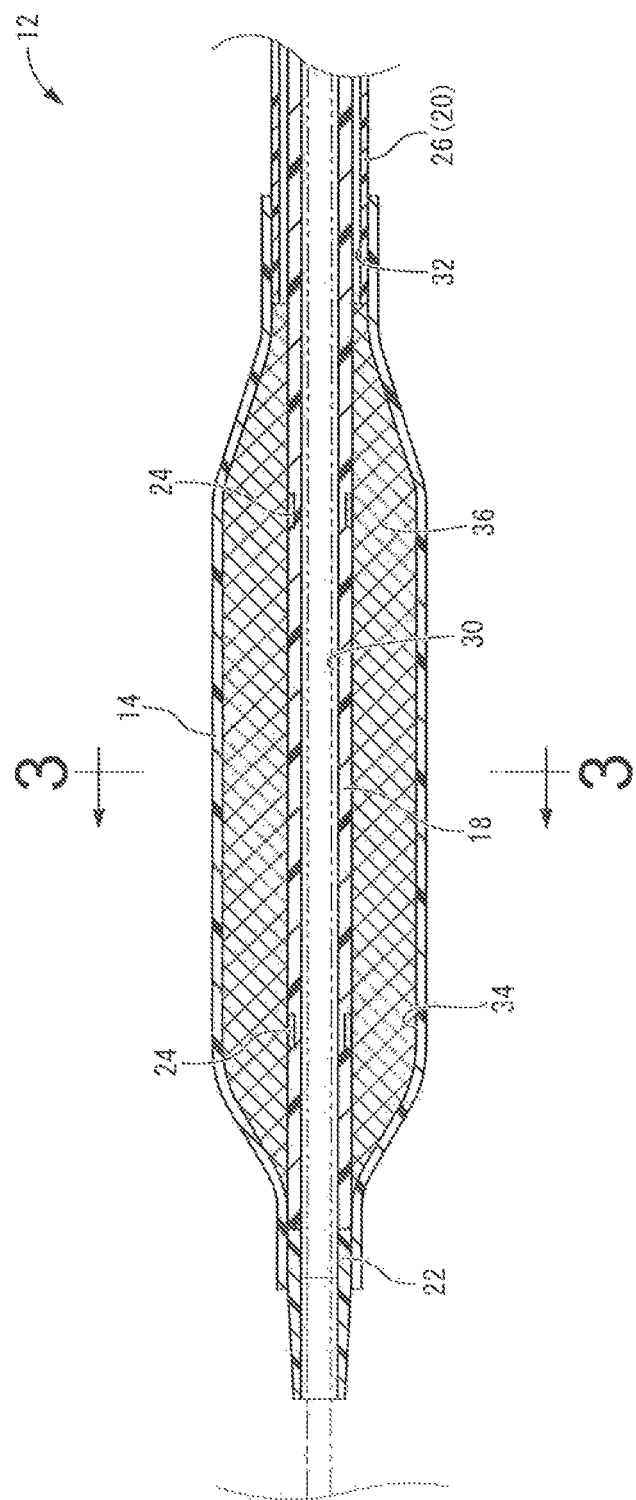
FIG. 2 is a longitudinal cross sectional view showing a distal end side of the balloon catheter shown in FIG. 1 when the balloon is expanded, as suitable for explaining a mode of an additional structure in the balloon.

More specifically, as FIG. 2 shows, the catheter 12 has a structure including double tubes wherein a tubular internal shaft 18 is inserted in a tubular external shaft 20.

Both the internal shaft 18 and the external shaft 20 can be formed with various materials and structures known conventionally as ones having characteristics with which they can be curved along the blood vessel. Specifically, each shaft can be formed of a synthetic resin material such as polyamide, vinyl chloride, polyurethane, polyimide, polyethylene, polyester elastomer, polypropylene, polytetrafluoroethylene, polyetheretherketone, polyvinylidene fluoride, a metallic material such as stainless steel, nickel-titanium alloy, and a combination of them.

The distal end part of the internal shaft 18 protrudes from the distal end of the external shaft 20 by a prescribed length. At the protruding end part of the internal shaft 18, a distal end tip 22 is attached. The distal end tip 22 is preferably softer than the internal shaft 18. For the distal end tip 22, the outer peripheral face has a tapered shape whose diameter gets gradually smaller as it goes toward the distal end side, and a central hole that communicates with the lumen of the internal shaft 18 is formed by piercing on the central axis thereof.

On the distal end part of the internal shaft 18 protruding from the external shaft 20, imaging markers 24, 24 are fixed. The imaging marker 24 is a member formed of a metallic material with radiopacity like a platinum-iridium alloy in an annular shape or a C character shape, and is fixed on the circumference wall of the internal shaft 18.

About the distal end part of the internal shaft 18 protruding from the external shaft 20, the balloon 14 is externally disposed. The balloon 14 is constituted by a tubular body formed by a film of a deformable synthetic resin material etc., for example, and the balloon 14 can undergo expanding/contracting deformation in the radial direction.

As the material of the balloon 14, materials known conventionally can be adopted. For example, polyethylene terephthalate, nylon, polyamide, polyether amide, polyether block amide copolymer, polyethylene, polyethylene elastomer, polypropylene, silicone rubber, latex rubber, and the like are preferably used.

When the balloon 14 of this embodiment expands, the balloon 14 takes a form wherein the axially middle part thereof is substantially a cylinder, while tapered tubes whose diameters get gradually smaller as they go to their respective outsides integrally extend out from the both axial ends of the axially middle part. When the balloon 14 contracts, the balloon 14 may collapse in an irregular fashion so as to reduce the diameter of its circumference wall. Alternatively, in the contraction, the balloon 14 can be set with a prescribed folded shape such that the balloon 14 is wrapped in the circumferential direction as folded at a plurality of locations on the circumference like an umbrella.

Both axial ends of the balloon 14 are fluidtightly fixed respectively on the outer peripheral face of the distal end side of the external shaft 20 and the outer peripheral face of the distal end side of the internal shaft 18, at the small-diameter side ends of the both tapered tubes. Thus, the balloon 14 defines an inside space on the outer peripheral face of the distal end side of the internal shaft 18, as tightly closed from the outside. In the space formed inside the balloon 14, the internal shaft 18 is disposed to pass through in the axial direction, while, inside the external shaft 20, a space formed on the outer peripheral face of the internal shaft 18 opens to be in communication.

Note that the balloon catheter 10 of this embodiment is a rapid exchange type. Specifically, the external shaft 20 has a structure wherein a distal shaft 26 and a proximal shaft 28 are connected to each other in the axial direction. The proximal end part of the internal shaft 18 inserted in the distal shaft 26 opens on the outer peripheral face of the connection section between the distal shaft 26 and the proximal shaft 28 or its proximity, at the middle portion in the lengthwise direction of the external shaft 20.

The inner lumen of the internal shaft 18 constitutes a guide wire lumen 30 for guide wire insertion. This guide wire lumen 30 extends from the distal end to the middle part of the catheter 12. That is, one end of the guide wire lumen 30 opens at the distal end of the catheter 12 through the distal end tip 22, while the other end opens on the outer peripheral face of the external shaft 20 at the middle part in the lengthwise direction thereof.

The inner lumen of the external shaft 20 constitutes a pressure regulating lumen 32 on the outer peripheral face of the internal shaft 18. This pressure regulating lumen 32 extends across about the whole length of the catheter 12. That is, the pressure regulating lumen 32 opens at the proximal end side of the proximal shaft 28 via the hub 16, and extends in the distal shaft 26 on the outer peripheral side of the internal shaft 18 with an annular cross section, and opens on the distal end face of the distal shaft 26 to communicate with the inside of the balloon 14.

Figure 3:
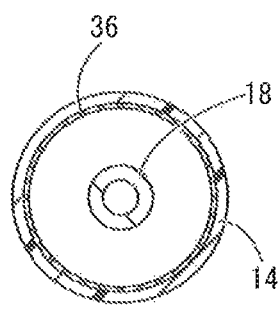
FIG. 3 is a cross sectional view taken along line 3-3 of FIG. 2.

Here, as FIGS. 2 and 3 show, an additional structure 36 is provided on an inner circumferential surface 34 of the balloon 14. For the additional structure 36 of this embodiment, the inner circumferential surface 34 of the balloon 14 is one formation surface, and it is directly formed on the inner circumferential surface 34. This allows the additional structure 36 to have a tubular mesh shape that is a substantially braid form as a whole, including two intersecting groups of spiral linear bodies, which are inclined to the opposite sides to each other relative to the circumferential direction. Specifically, the additional structure 36 of this embodiment is a tubular body that is continuous in the circumferential direction and the axial direction as a whole, by the plurality of linear bodies extending in the axial direction while slanting with a prescribed angle relative to the circumferential direction.

According to the additional structure 36 of this mesh shape, by deformation of each linear body, expanding/contracting deformation can be advantageously allowed. Therefore, although the additional structure 36 remains secured on the inner circumferential surface of the balloon 14, the expanding/contracting deformation of the balloon 14 is permitted.

In the present embodiment, across almost all of the inner circumferential surface 34 of the balloon 14, the mesh-shaped additional structure 36 is disposed. However, the disposition location, the size of the disposition area, and the like for the additional structure 36 are not limited. For example, the additional structure 36 can be disposed only in the tubular axially central part of the balloon 14 for which pressure deformation tends to become large in expansion of the balloon 14.

For this additional structure 36, the diameter of each linear body, the mesh size, and the like can be adjusted as appropriate depending on the required characteristics for the balloon catheter 10, under no limitation. In the same way, the material of the additional structure 36 can be selected, and ceramics, synthetic resins and the like can be adopted. Preferably, the additional structure 36 formed of a metal-based material by electroforming, etching, thermal spraying, vacuum deposition, or the like is adopted. Alternatively, the additional structure 36 formed of a resin-based material by thermal spraying, vacuum deposition, or the like is used.

By forming the additional structure 36 directly on the inner circumferential surface 34 of the balloon 14, the additional structure 36 can be secured to the balloon 14 with some force. For example, by providing a resin layer or an adhesive layer as suitable on the inner circumferential surface 34 of the balloon 14 in advance, it is possible that the additional structure 36 is not adhered to the inner circumferential surface 34 of the balloon 14, or that the additional structure 36 is more securely adhered thereto. Moreover, it is also possible to mix a curable metal paste layer that forms the additional structure 36 through thermal spraying, vacuum deposition, or the like, with a resin material that exhibits a fixation force in relation to the balloon 14, thereby improving the fixation force of the additional structure 36 to the balloon 14.

In the balloon catheter 10 of the present embodiment wherein the above-described additional structure 36 is provided on the inner circumferential surface of the balloon 14, by being formed on the surface of the balloon 14, the additional structure 36 whose shape precisely corresponds to the shape of the balloon 14 can be stably provided. This makes it possible to effectively and stably exert the improvement effect of the pressure resistance and the strength for the balloon 14 by the additional structure 36.

The additional structure 36 is formed by electroforming, etching, or the like, so that it can be provided with free setting for the shape, the dimension, and the disposition location, without limitation to the tubular shape like the conventional structure. Besides, since a high dimension accuracy can be obtained, the performance can be stably attained, whereby the target performance like improvement in the pressure resistance, the strength, the durability and the like in relation to the balloon 14 is favorably exhibited.

The network structure, the spiral structure or the like shown in the aforesaid embodiment is formed with the intersection structure of linear bodies with a width thin enough, so that it is also possible to get soft deformation performance of the additional structure 36. Thus, insertion easiness of the balloon catheter in relation to the blood vessel can be kept well without considerably hampering the expanding/contracting deformation of the balloon.

In this embodiment, the additional structure 36 is formed on the inner circumferential surface of the balloon 14. Thus, the balloon catheter 10 has the structure wherein the additional structure 36 is covered by the balloon 14, thereby preventing direct contact of the additional structure 36 with body tissues like the blood vessels, and hence the resultant problems. This leads to another advantage of securing a great degree of freedom in selection for the material, the shape, and the like of the additional structure 36.

The embodiment of the present invention has been described above, but this invention is not interpreted in a limited way by the specific description in the above-mentioned embodiment etc. In the present invention, for forming the additional structure, some of various arts including electroforming, etching, thermal spraying, and vacuum deposition can be used in combination, for example. Besides, by utilizing these film production techniques, the additional structure may be formed with a layered structure of different materials by performing a plurality of electroforming works, or the like.

As the specific shape of the additional structure, the linear body having the above-described linear shape that is continuous in the lengthwise direction of the balloon, the tubular body having a spiral linear shape like a coil spring, or the tubular body of the network structure including two intersecting groups of plural spiral linear shapes, which are inclined to opposite sides to each other relative to the circumferential direction, wherein the two groups are integrally linked at the intersection parts (see FIG. 2) is used. Besides, it is also possible to adopt the additional structure formed on the basis of a curved linear shape extending in the circumferential direction with a repetitive wave form, for example.

In the aforementioned embodiment, the additional structure 36 is provided on the inner circumferential surface of the balloon 14, but it can be formed on the outer circumferential surface of the balloon 14, instead of or in addition to the inner circumferential surface of the balloon 14. By forming the additional structure 36 on the outer circumferential surface of the balloon 14, the expanding deformation of the balloon 14 acts to a direction such that the expansion pushes the balloon 14 on the additional structure. Therefore, the improvement effect for the pressure resistance performance of the balloon by the additional structure is even more effectively exhibited, while the secured state of the additional structure in relation to the balloon can be more stably retained.

It is possible to perform cooling treatment of the balloon 14 as appropriate when forming the additional structure on the surface of the balloon 14, considering the adopted forming method, material, and the like. This cooling treatment can be, for example, cooling control of the atmosphere temperature. Alternatively, it is possible to have a cooling fluid that flows by circulation or convection flow in contact with the outer circumferential surface or the inner circumferential surface of the balloon 14 on the side opposite to the formation surface of the additional structure for cooling.

As the additional structure, other than the above-mentioned mesh structure and spiral structure, it is also possible to use a linear body extending independently, as parallel to the axial direction or as inclined by a prescribed angle. In this case, a single linear body or a plurality of linear bodies may be disposed on the inner circumferential surface or the outer circumferential surface of the balloon 14.

Figure 4:
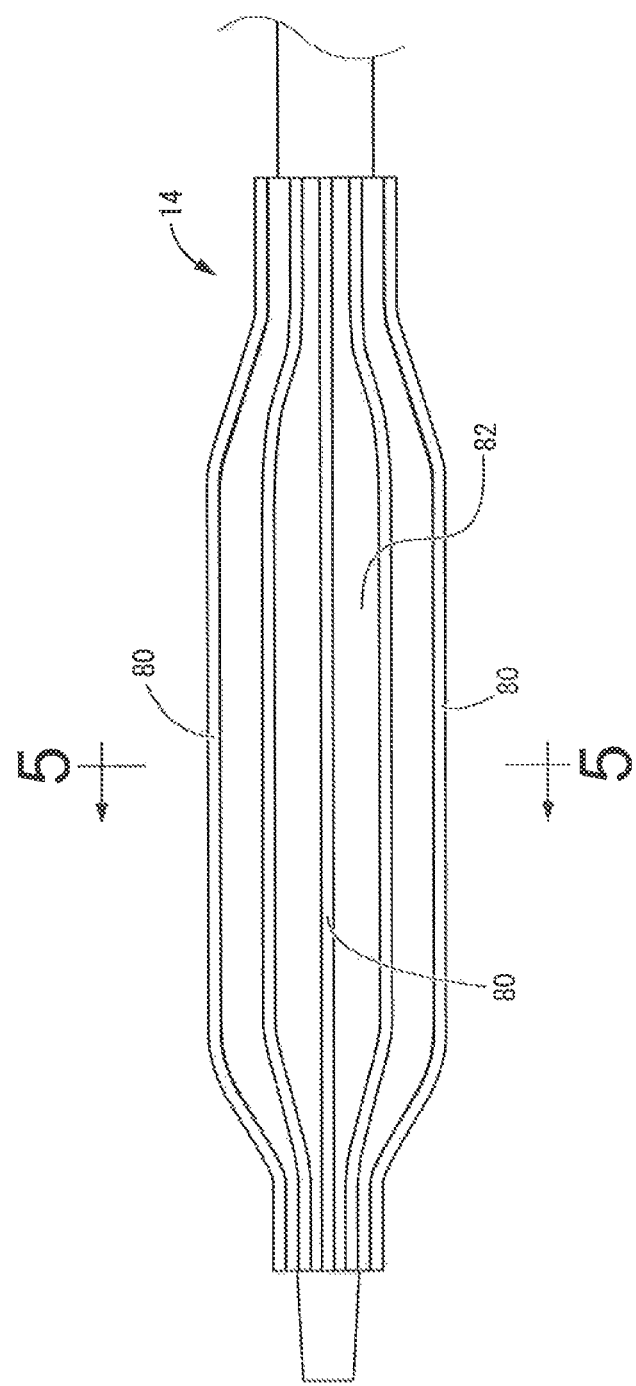
FIG. 4 is an outside view showing the distal end side of the balloon catheter as another embodiment of the present invention when the balloon is expanded, as suitable for explaining another mode of the additional structure.
Figure 5:
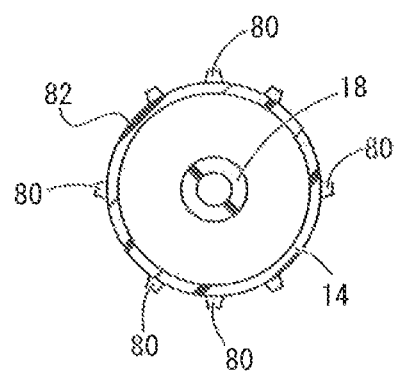
FIG. 5 is a cross sectional view taken along line 5-5 of FIG. 4.

Specifically, for example as FIG. 4 shows, it is possible to provide additional structures 80 comprising linear bodies that extend linearly as parallel to the axial direction on the outer circumferential surface of the balloon 14. As FIG. 5 shows, these additional structures 80 are formed to project on an outer circumferential surface 82 of the balloon 14, thereby constituting blades. Note that the additional structures 80 can be formed directly on the outer circumferential surface 82 of the balloon 14 by electroforming etc., as well as the above-cited embodiment.

In the embodiment shown in FIGS. 4 and 5, the additional structures 80 can be provided as the blades projecting on the outer circumferential surface of the balloon 14. Owing to these additional structures 80, the reinforcement effect of the balloon 14 can be attained, while the balloon 14 can be constituted as a cutting balloon. Each additional structure 80, which extends in the axial direction, may be inclined only by a prescribed angle with respect to the circumferential direction, and it may have convex and concave portions like a saw blade in its projecting tip. Additionally, it is possible as well to provide a ring-shaped connection part that extends in the circumferential direction to connect the plurality of additional structures 80 with one another.

The additional structure with the prescribed pattern that may be various shapes including mesh shape and linear shape can be formed on either or both of the outer circumferential surface and the inner circumferential surface of the balloon.

Adopted in the above-mentioned embodiment is a rapid exchange type of catheter wherein the proximal end side of the guide wire lumen 30 opens on the outer circumferential surface of the catheter 12. Alternatively, it is possible to use an over-the-wire type of catheter wherein the proximal end side of the guide wire lumen opens to the outside via the hub 16 provided at the proximal end side of the external shaft 20.

In addition to them all, other embodiments including various changes, amendments, modifications and the like on the basis of the knowledge of the skilled person, which are not recited one by one, can be used to realize the present invention. Needless to say, as long as these embodiments do not deviate from the concept of this invention, they are all included in the range of the present invention.

KEYS TO SYMBOLS

10: Balloon catheter; 12: Catheter; 14: Balloon; 16: Hub; 18: Internal shaft; 20: External shaft; 22: Distal end tip; 34: Inner circumferential surface; 36, 80: Additional structure; 82: Outer circumferential surface

The invention claimed is:

1. A method of manufacturing a balloon catheter including a balloon provided on a distal end side of a shaft, comprising:
   forming the balloon of a deformable synthetic resin;
   applying a curable metal paste layer with a resin material mixed therein to a formation surface of the balloon so as to form an additional structure directly on the formation surface as a result of the application, wherein the applying comprises at least one of thermal spraying and vacuum deposition, the resin material exhibits a fixation force in relation to the balloon, the additional structure is formed in a prescribed pattern directly on the formation surface, and the formation surface is a surface of at least one of an inner circumferential surface of the balloon and an outer circumferential surface of the balloon; and
   performing cooling treatment of the balloon to a surface opposite the formation surface of the balloon during the applying via at least one of thermal spraying and vacuum deposition.

2. The method of manufacturing a balloon catheter according to claim 1, wherein the additional structure is formed on the inner circumferential surface of the balloon.

3. The method of manufacturing a balloon catheter according to claim 1, wherein the additional structure has a tubular mesh shape that is continuous in a circumferential direction of the balloon.

4. The method of manufacturing a balloon catheter according to claim 1, wherein the additional structure has a linear shape that is continuous in a lengthwise direction of the balloon.

5. The method of manufacturing a balloon catheter according to claim 4, wherein the additional structure includes a plurality of continuous non-intersecting linear bodies extending in the lengthwise direction of the balloon.

6. The method of manufacturing a balloon catheter according to claim 5, wherein the plurality of continuous non-intersecting linear bodies are formed on the outer circumferential surface of the balloon and configured as blades.

7. The method of manufacturing a balloon catheter according to claim 1, wherein the additional structure is deformable due to expansion and contraction of the balloon.

8. The method of manufacturing a balloon catheter according to claim 1, wherein the additional structure is secured on at least one of the inner circumferential surface and the outer circumferential surface of the balloon.

9. The method of manufacturing a balloon catheter according to claim 1, wherein the additional structure includes a plurality of intersecting spiral linear bodies.

10. The method of manufacturing a balloon catheter according to claim 9, wherein the plurality of intersecting spiral linear bodies are slanted at a prescribed angle relative to a circumferential direction of the balloon.

11. The method of manufacturing a balloon catheter according to claim 1, wherein the additional structure includes a first additional structure formed directly on the inner circumferential surface of the balloon and a second additional structure formed directly on the outer circumferential surface of the balloon.

12. The method of manufacturing a balloon catheter according to claim 1, wherein the additional structure is formed by a combination of thermal spraying and vacuum deposition.

* * * * *